US005750072A

United States Patent [19]

Sangster et al.

[11] Patent Number: 5,750,072

[45] Date of Patent: May 12, 1998

[54] STERILIZATION BY MAGNETIC FIELD STIMULATION OF A MIST OR VAPOR

[76] Inventors: Bruce Sangster, 8252 Delfino Cir., Huntington Beach, Calif. 92646; James D. Bond, 3857 Birch St. Ste 556, Newport Beach, Calif. 92660

[21] Appl. No.: 790,754

[22] Filed: Jan. 27, 1997

Related U.S. Application Data

[63] Continuation-in-part of Ser. No. 514,697, Aug. 14, 1995, abandoned.

[51] Int. Cl.$^6$ .................... A61L 2/02; A61L 2/16; C12N 13/00

[52] U.S. Cl. .................... 422/22; 422/28; 422/292; 435/173.1; 435/173.5

[58] Field of Search .................... 422/22, 28, 292; 435/173.1, 173.5

[56] References Cited

U.S. PATENT DOCUMENTS

| | | | |
|---|---|---|---|
| 3,837,915 | 9/1974 | Erb | 134/1 |
| 3,876,373 | 4/1975 | Glyptis | 422/22 X |
| 4,524,079 | 6/1985 | Hofmann | 422/22 X |
| 4,670,010 | 6/1987 | Dragone | 422/292 X |
| 5,074,322 | 12/1991 | Jaw | 422/292 X |
| 5,264,102 | 11/1993 | Eibl | 204/302 |

FOREIGN PATENT DOCUMENTS

| | | |
|---|---|---|
| 4-152873 | 5/1992 | Japan . |

*Primary Examiner*—Timothy McMahon
*Assistant Examiner*—E. Leigh McKane
*Attorney, Agent, or Firm*—Gene Scott - Patent Law & Venture Group

[57] ABSTRACT

A sterilization process is disclosed which utilizes an oscillating magnetic field to control the state of free radicals in a sterilizing media and which synergetically induces a molecular structural change in the microorganism, thereby increasing the vulnerability of the microorganism to the sterilizing media. This process significantly enhances the efficiency of the sterilizing media and reduces the exposure time necessary for a lethal dose to harmful microorganisms. It is also disclosed that this process can be used directly on living human tissue or fragile medical devices or implants with no detrimental effects to the patient. It is also disclosed that this process can be used on the hands of health care or food service personnel to reduce the likelihood of nosocomial infection.

12 Claims, 3 Drawing Sheets

STERILIZATION BY MAGNETIC FIELD STIMULATION OF A MIST OR VAPOR

This application is a continuation in part of application Ser. No. 8/514,697 fild Aug. 14, 1995, now abandoned.

BACKGROUND OF THE INVENTION

1. Field of the Invention

This invention relates generally to systems, devices and methods for rendering viruses, bacteria, fungi and other harmful microorganisms ineffective and more specifically provides a novel apparatus and method for sterilization that excludes high heat, radiation, and toxic gases which are harmful to human skin, tools and devices.

2. Description of Related Art

Although no prior art has been identified pertaining to the use of magnetic fields in combination with sterilizing fluids as in the present invention, there is a substantial body of prior art which relates to the use of electromagnetic fields in plasma sterilization processes which employ a gas of ionized charged particles in a closed chamber to effect sterilization. An optional method described in prior art is the use of alternating electromagnetic fields to create a sufficient heat energy in the microorganism to produce a lethal effect. It is clear, this protocol could not be used directly on human skin due to the associated damage to the skin and tissue of the patient caused by the heating. We have therefore excluded from this review of prior art any patents for sterilization which utilize various techniques (steam, eddy current, microwave energy) to create an elevated temperature in order to sterilize. These protocols create excited molecules, free radicals and charged energy levels which cannot be applied directly to living human tissue.

The following art most directly defines the present state of this field:

Dragone, U.S. Pat. No. 4,670,010 describes an invention that concerns the technical field of apparatus for dispensing liquids over different parts of the human body, either for disinfecting or therapeutic purposes, and relates to a liquid-nebulizing device for the dermatological treatment of the hands.

Jaw, U.S. Pat. No. 5,074,322 describes an invention for sterilizing and air-drying the user's hands, a sterilizing hand dryer comprising an antiseptic solution spraying system for discharging antiseptic solution through a nozzle to sterilize the body limb inserted in a sterilizing chamber and detected by an electric eye, a hot air blower means for discharging hot air in said sterilizing chamber for drying said body limb, a control circuit for stopping the sterilizing hand dryer 3 seconds after removal of said body limb from said sterilizing air bath camber.

Hofmann, U.S. Pat. No. 4,524,079 describes material having relatively high electrical resistivity, such as food products and containers, is disposed within a magnetic coil and subjected to one or more pulses of an oscillating magnetic field having an intensity of between about 2 and about 100 Tesla and a frequency of between about 5 and about 500 kHz. A single pulse of the magnetic field generally decreases the microorganism population by at least about two orders of magnitude, and substantially complete sterility is more closely approached by subjecting the material to additional pulses.

Eibl, U.S. Pat. No. 5,264,102 describes apparatus for the treatment of an aqueous liquid includes a flat, cylindrical treatment chamber made of electrically insulating material. Two flat electrode plates are disposed parallel to and spaced from each other in opposite side walls of the treatment chamber. Each electrode plate is insulated from the liquid by a thin layer of electrical insulation. One terminal of a d.c. high voltage source is connected to the electrode plates so that the same voltage is applied to both plates. The opposite terminal of the voltage source is connected to electrically conductive means in direct contact with the liquid so that an electrostatic field is established between the two electrode plates and the liquid itself.

The prior art teaches the use of sterilizing fluids and of electrical induction of changes to such liquids for the purpose of improved sterilization. However, the prior art does not teach a system and method of operation as presented which provides further related advantages as described in the following summary.

SUMMARY OF THE INVENTION

The present invention teaches certain benefits in construction and use which give rise to the objectives described below.

The present invention teaches a sterilization apparatus and method providing a modulated magnetic field through which is directed a fine mist or vapor of a sterilizing fluid for producing free radical states in the mist or vapor and therefore on a workpiece inserted into the mist or vapor. Accordingly, several objects and advantages of the invention are the control of reactivity of a sterilizing fluid, for example hydrogen peroxide, so that the sterilizing effect is significantly enhanced by the maintenance of molecules in a free radical state. A synergistic advantage provided by the oscillating magnetic field is the change in bacterial, fungal and viral structure induced by the field. At selected frequencies of the magnetic field, the microorganisms open their molecular structure to become more vulnerable to the effect of the sterilizing fluid. An additional advantage is the ability to utilize the combined magnetic field and sterilizing fluid directly on living human tissue, or devices which are too fragile to be exposed to other sterilizing mediums or methods.

The combination of a low energy magnetic field and a sterilizing fluid having low toxicity provides the advantage of using the present protocol under many different conditions thereby providing for diverse applications. This system may be employed for hand sterilization, or tools and other general applications, and may also be used on laser endoscopes, catheters, or other devices which are utilized in invasive patient treatment procedures. The present sterilizing method does not necessarily utilize or generate any heat to effect sterilization, and therefore can be used to sterilize any object or workpiece that is non-magnetic.

The principal objective of the present invention is to provide a sterilization method which is effective without using high temperature, toxic chemicals, harmful radiation or high electromagnetic energy levels.

It is another objective of this invention to provide a sterilization method which can be used directly on living human tissue.

It is another objective of this invention to provide a sterilization method which can be used on fragile medical devices which are utilized in invasive procedures, such devices be exemplified by catheters, endoscopes and biopsy tools.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE PREFERRED EMBODIMENT

Figure 1:
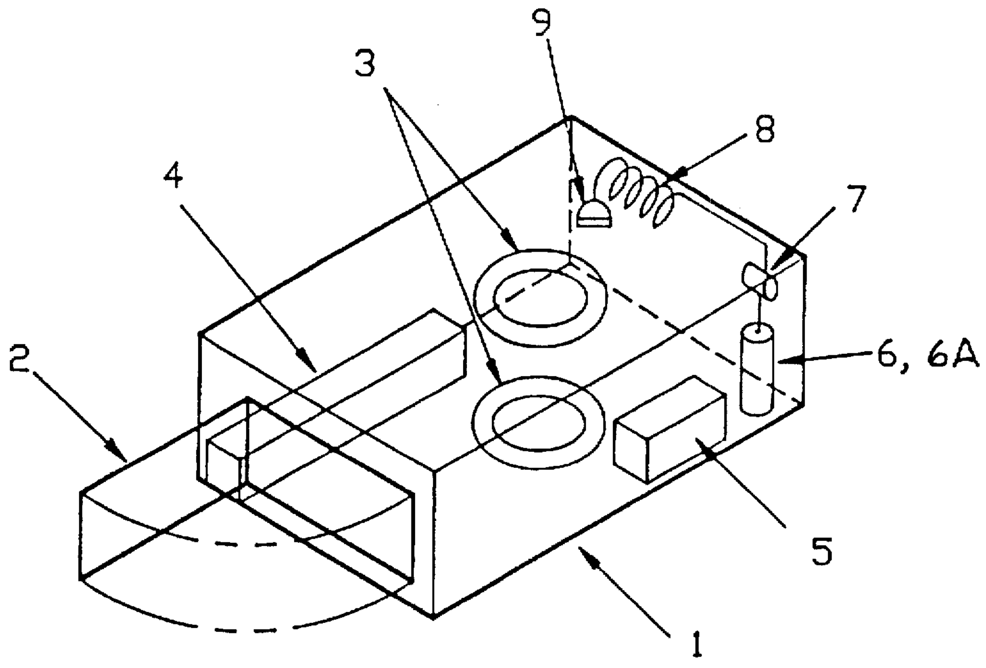
FIG. 1 is a perspective mechanical schematic view of a preferred embodiment of the present invention defining the preferred location of the important components therein.

The above described drawing figures illustrate the invention, a system and method for sterilization. As seen in FIG. 1, the present invention includes several necessary components including two or more Helmholz type coils 3, each having a diameter large enough to effectively couple to a workpiece to be sterilized, a source of alternating electrical current 4 and a modulator 5 to provide pulsed electrical energy to the Helmolz coils 3. The frequency of modulation is preferably within the range 100 HZ to 10 KHZ as it has been determined that this range provides the advantages of the invention. Another necessary component is a spray misting or vaporizing apparatus including a fluid storage bottle 6 and a pump 7 capable of pressurizing a sterilizing fluid 6*a* within the bottle 6, such as hydrogen peroxide, to a sufficient pressure to eject the fluid through a means bar disbursing such as one or more spray nozzles 9 in order to coat the surface of objects to be sterilized with a thin layer of droplets of the sterilizing fluid mist or condensate from the vapor.

In use, the surfaces to be sterilized, such as surfaces of the hands of a worker, tissue samples, and other non-metal tools or parts, are exposed to an oscillating magnetic field in the milli-Tesla range and the spray mist or vapor of the sterilizing fluid for a period sufficient to provide a lethal effect to microorganisms. This process is based on the experimental evidence that an oscillating external magnetic field changes the share of singlet and triplet electronic states in the total energy state of a pair of radicals in solution. By varying the oscillating frequency, the reaction rate of recombination of the free radicals can be fixed, thus providing a continuing exposure of the free radical to the surface to be sterilized. Such free radicals are deadly to microorganisms. A synergistic benefit of the oscillating magnetic field is the change induced in bacterial, fungal and viral molecular structures by the field's energy. It has been discovered that at selected frequencies, in the range of 100 HZ to 10 KHZ, the molecular structures of microorganisms are induced to change to a more open structure. This puts the microorganisms in a vulnerable state so they are more subject to the effect of the sterilizing fluid.

Unlike other external factors such as electrode created electromagnetic charge or microwave energy in, or above the radio frequency bands, or ultraviolet radiation used in other sterilization methods, the present magnetic field process produces little or no ancillary effects or disturbances but is highly effective in its effect to the electronic states of the molecules and atoms of the sterilizing fluid. This is due to the fact that the electronic energy state change in a magnetic filed is much less than the thermal energy state change. Therefore by proper selection of frequency and intensity, the sterilizing fluid can be maintained in a state of free radicals for as long as fluid is available. This factor provides a substantial advantage over other types of free radical sterilization processes such as plasma, because the free radicals are in a fixed state at a lower energy and thereby require less time and energy to effect the sterilization. Also, because the process does not utilize any toxic fluids, heating of the workpiece or high energy irradiation, it can be used directly on human tissue or fragile medical elements.

Accordingly, the invention provides a substantial advantage in usefulness over other sterilization methods such as plasma or irradiation with microwaves and because of its protocol, can be used safely on living tissue or medical devices without detrimental effects.

The present invention is more specifically and particularly defined as follows:

As best seen in FIG. 1, the invention is a sterilization and disinfecting system for use with a sterilizing fluid 6A on a workpiece (not shown). The system includes a means for pressurizing 7 of the sterilizing fluid 6A so as to direct the fluid 6A to a means for disbursing 9, which is positioned relative to the workpiece so that the fluid 6A is directed as a fine mist or vapor toward the workpiece. The means for pressurizing the sterilizing fluid 7 is preferably a fluid pump of any common type suitable for such result and well known in the art. The means for disbursing 9 is any common type of misting nozzle or vapor directing nozzle, which is known in the art, capable of receiving the sterilizing fluid 6A as a liquid and producing a fine mist or vapor ejected within the enclosure 1. Such a means for disbursing 9 may be one or more of such nozzles. The means for directing the fluid from the sterilizing liquid container 6 to the spraying means 9 may be any type of well known fluid tubing or pipe system constructed for interconnecting the above components of the invention and would be easily constructed by those of skill in the art without direction herein.

An amplifier means 4, of any suitable and common and well known type, generates an electric signal in communication with an electronic modulation means 5, again of a suitable type known in the art, for modulating the electric signal with a frequency preferably between 100 HZ and 10 KHZ. A magnetic coil means 3, preferably a pair of opposing Helmholtz coils, receives the modulated electric signal and generates a magnetic field between them in which the workpiece is immersed, the magnetic field maintaining molecules of the mist or vapor in a free radical state for sterilizing and disinfecting the workpiece. The above described components are preferably housed in an enclosure means 1 of a suitable size and shape for containing and associating the mist with the workpiece. A means for heating 8 of the sterilizing fluid 6A into a vapor phase may be employed in the invention and has been found to be effective in certain applications, but is not necessary in all applications. Such a heating means 8 may be any suitable heating device and method as is well known in the art such as electrical heating. In the case that the fluid 6A is vaporized it condenses onto the workpiece and typically forms a thinner and more continuous layer then when a mist is used.

Figure 2:
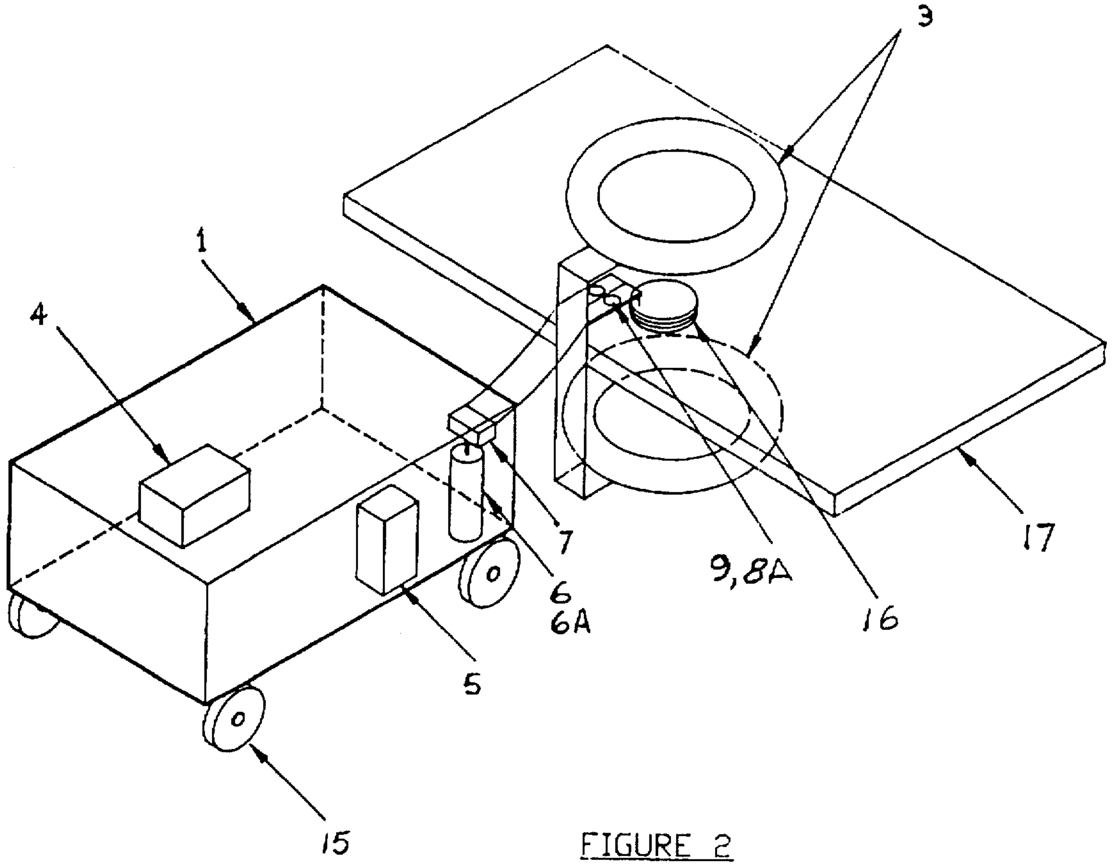
FIG. 2 is a perspective mechanical schematic view of an alternate preferred embodiment of the present invention for use in applications at a surgical site and defining the preferred location of the important components therein.
Figure 3:
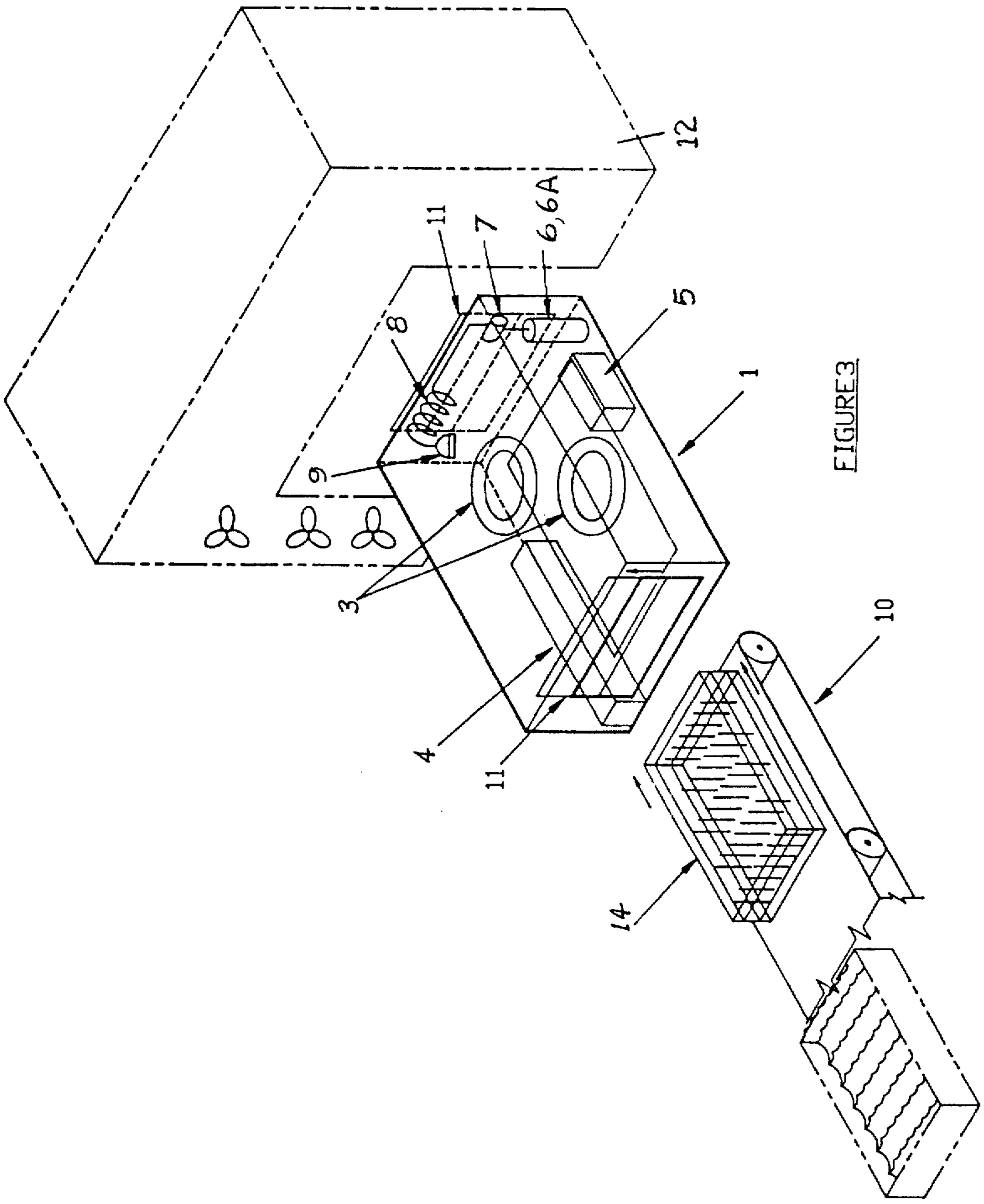
FIG. 3 is a perspective mechanical schematic view of another alternate preferred embodiment of the present invention for use in a continuous sterilizing operation and defining the preferred location of the important components therein.

The enclosure means 1 may have a single entrance or aperture for the insertion of the workpiece as is shown in FIG. 1 with applications to sterilization of the hands, tools and other workpieces of interest. The enclosure means I may also provide at least two opposing apertures as shown in FIG. 3 for entry and exit of the workpiece in a continuous process whereby the workpiece passes through the enclosure 1. In this case a workpiece holder 14 such as a basket is conveyed on a means for conveyance 10 to enter a sliding door 11 into the enclosure 1. The holder 14 then passes through the enclosure 1 and out of a second sliding door 11 into a dryer 12. As shown in FIG. 2 a setup similar to that shown in FIG. 1 is employed except that the disbursing means 9 and the coil means 3 are positioned external to the enclosure I so as to sterilize a surgical site or other similar application. In FIG. 2 is shown a surgical bed 17 upon which a patient might be laid. The coil means 3 is positioned as shown and the heating and disbursing means 8A, and 9 respectively are positioned adjacent to the operating site. A flexible sealing enclosure 16, such as a plastic bellows, may be used to contain the disbursed fluid or vapor and to help direct it toward the site of a patient's wound.

The method of sterilizing and disinfecting employed in the system apparatus described above includes preferred steps. These steps include: providing the sterilizing fluid 6A and the workpiece to be sterilized, pressurizing the sterilizing fluid 6A so as to direct the fluid to the means for disbursing 9, positioning the means for disbursing 9 relative to the workpiece so that the sterilizing fluid 6A is directed as a fine mist or vapor toward the workpiece, amplifying the electric signal, modulating the electric signal preferably at a frequency of between 100 HZ and 10 KHZ, applying the modulated electric signal to the magnetic coil means for generating the magnetic field, preferably in the milli-Tesla range, and finally applying the magnetic field to the mist or vapor to create free radicals on the workpiece for sterilizing and disinfecting the workpiece. As stated the method may employ the step of moving the workpiece into the mist or vapor and thereafter, out of the mist or vapor in a continuous process as shown in FIG. 3. In an alternate approach, as shown in FIG. 2, the means for disbursing 9 and the magnetic coil means 3 are positioned external to the enclosure 1 such that they are positionable adjacent to a surgical site.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A sterilization and disinfecting system for use with a sterilizing fluid on a workpiece at atmospheric pressure, the system comprising:

a means for pressurizing the sterilizing fluid so as to direct the fluid to a means for disbursing;

the means for disbursing being positioned relative to the workpiece so that the sterilizing fluid is directed toward the workpiece;

amplifier means for generating an electric signal in communication with an electronic modulation means for modulating the electric signal;

magnetic coil means for receiving the modulated electric signal and for applying an oscillating magnetic field to the workpiece, the magnetic field maintaining the sterilizing fluid in a free radical state for sterilizing and disinfecting the workpiece.

2. The system of claim 1 further including an enclosure means for containing and associating the mist with the workpiece.

3. The system of claim 2 wherein the enclosure means provides at least two opposing apertures for entry and exit of the workpiece in a continuous process.

4. The system of claim 1 further including a means for heating the sterilizing fluid to a vapor.

5. The system of claim 1 wherein the modulation means operates in the frequency range of between 100 HZ and 10 KHZ.

6. The system of claim 1 wherein the sterilizing fluid is ejected by the disbursing means as a mist.

7. A method of sterilizing and disinfecting comprising the steps of:

a) providing a sterilizing fluid and a workpiece to be sterilized;

b) pressurizing the sterilizing fluid so as to direct the fluid to a means for spraying;

c) positioning the means for spraying relative to the workpiece so that the sterilizing fluid is directed as a fine mist toward the workpiece;

d) amplifying an electric signal;

e) modulating the electric signal;

f) applying the modulated electric signal to a magnetic coil means for generating an oscillating magnetic field;

g) applying the oscillating magnetic field to the mist to create free radicals on the workpiece for sterilizing and disinfecting the workpiece.

8. The method of claim 7 further including the step of moving the workpiece into the mist and thereafter, out of the mist in a continuous process.

9. The method of claim 7 wherein the frequency of modulation in step (e) is between 100 HZ and 10 KHZ.

10. A method of sterilizing and disinfecting comprising the steps of:

a) providing a sterilizing fluid and at atmospheric pressure, a workpiece to be sterilized;

b) pressurizing the sterilizing fluid so as to direct the fluid to a means for heating the fluid to a vapor;

c) positioning a means for vapor ejection relative to the workpiece so that the sterilizing fluid is directed as a vapor toward the workpiece;

d) amplifying an electric signal;

e) modulating the electric signal;

f) applying the modulated electric signal to a magnetic coil means for generating an oscillating magnetic field;

g) applying the oscillating magnetic field to the vapor to create free radicals on the workpiece for sterilizing and disinfecting the workpiece.

11. The method of claim 10 further including the step of moving the workpiece into the vapor and thereafter, out of the vapor in a continuous process.

12. The method of claim 10 wherein the frequency of modulation in step (e) is between 100 HZ and 10 KHZ.

* * * * *